(12) United States Patent
Boles et al.

(10) Patent No.: US 6,759,196 B2
(45) Date of Patent: Jul. 6, 2004

(54) METHOD OF DETECTING MITOCHONDRIAL DYSFUNCTION

(75) Inventors: Richard G. Boles, Pasadena, CA (US); Masamichi Ito, Chestnut Hill, MA (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 0 days.

(21) Appl. No.: 09/791,125

(22) Filed: Feb. 22, 2001

(65) Prior Publication Data

US 2003/0165827 A1 Sep. 4, 2003

Related U.S. Application Data

(60) Provisional application No. 60/184,379, filed on Feb. 23, 2000.

(51) Int. Cl.[7] .................. C12Q 1/68; C12P 19/34; C07H 21/04
(52) U.S. Cl. .................. 435/6; 435/91.1; 536/23.1; 536/24.3
(58) Field of Search .................. 435/6, 91.1, 91.2, 435/366; 536/23.1, 24.3, 24.33

(56) References Cited

U.S. PATENT DOCUMENTS 5,464,945 A    11/1995  Reynolds et al.
5,569,754 A    10/1996  Williams et al.
6,344,322 B1 *  2/2002  Polyak et al.

OTHER PUBLICATIONS

Siguroardottir et al; Am. J. of Human Genet. vol. 66, pp 1599–1609, 2000.*
Meyer et al Genetics, vol. 152, pp 1103–1110, 1999.*
Stoneking ; Am. J. of Human Genet. vol. 67, pp 1029–1032, 2000.*
Piercy et al (nternational Journal of Legal Medicine, vol. 106, pp 85–90, 1993.*
Dimo–Simonin et al; International Journal of Legal Medicine, vol. 113, pp 89–97, 2000.*
Graven et al; Molecular Biology and Evolution, vol. 12, pp 334–345, 1995.*
Marchington et al ; Human Molecular Genetics, vol. 5, pp 473–479, 1996.*
Poulton et al,; Diabetologia, vol. 41, 1998, pp 54–58.*
"DNA Profiling" from DNA Diagnostics Inc. : www.dnadiagnositicsinc.com/dnaprofiling.html; 2002.*

* cited by examiner

*Primary Examiner*—Jehanne Sitton
(74) *Attorney, Agent, or Firm*—Myers Bigel Sibley & Sajovec (57) ABSTRACT

A method of screening a subject for mitochondrial dysfunction comprises detecting the presence or absence of single nucleotide changes in a hypervariable region of the mitochondrial DNA of said subject, the presence of such changes indicating that said subject is afflicted with or at risk of developing mitochondrial dysfunction.

13 Claims, 3 Drawing Sheets

SEQUENCE LISTING

<160> NUMBER OF SEQ ID NOS: 10

<210> SEQ ID NO 1
<211> LENGTH: 21
<212> TYPE: DNA
<213> ORGANISM: synthetic construct

<400> SEQUENCE: 1
cacccaaagc taagattcta a                                              21

<210> SEQ ID NO 2
<211> LENGTH: 21
<212> TYPE: DNA
<213> ORGANISM: synthetic construct

<400> SEQUENCE: 2
aggctttatg accctgaagt a                                              21

-continued

```
<210> SEQ ID NO 3
<211> LENGTH: 21
<212> TYPE: DNA
<213> ORGANISM: synthetic construct

<400> SEQUENCE: 3
tccacatcaa aaccccccc c                                              21

<210> SEQ ID NO 4
<211> LENGTH: 21
<212> TYPE: DNA
<213> ORGANISM: synthetic construct

<400> SEQUENCE: 4
aggctttatg accctgaagt a                                             21

<210> SEQ ID NO 5
<211> LENGTH: 21
<212> TYPE: DNA
<213> ORGANISM: synthetic construct

<400> SEQUENCE: 5
tctccctaat tgaaaacaaa a                                             21

<210> SEQ ID NO 6
<211> LENGTH: 21
<212> TYPE: DNA
<213> ORGANISM: synthetic construct

<400> SEQUENCE: 6
tggattgggt ttttatgtac t                                             21

<210> SEQ ID NO 7
<211> LENGTH: 21
<212> TYPE: DNA
<213> ORGANISM: synthetic construct

<400> SEQUENCE: 7
cctccgtgaa atcaatatcc c                                             21

<210> SEQ ID NO 8
<211> LENGTH: 21
<212> TYPE: DNA
<213> ORGANISM: synthetic construct

<400> SEQUENCE: 8
aaactgtggg gggtgtcttt g                                             21

<210> SEQ ID NO 9
<211> LENGTH: 21
<212> TYPE: DNA
<213> ORGANISM: synthetic construct

<400> SEQUENCE: 9
cccatcctac ccagcacaca c                                             21

<210> SEQ ID NO 10
<211> LENGTH: 21
<212> TYPE: DNA
<213> ORGANISM: synthetic construct

<400> SEQUENCE: 10
gatatgaagc accgccaggt c                                             21
```

METHOD OF DETECTING MITOCHONDRIAL DYSFUNCTION

RELATED APPLICATIONS

This application claims the benefit of U.S. Provisional Application Serial No. 60/184,379, filed Feb. 23, 2000, the disclosure of which is incorporated by reference herein in its entirety.

FIELD OF THE INVENTION

The present invention relates to methods of screening subjects for mitochondrial dysfunction.

BACKGROUND OF THE INVENTION

A wide variety of clinical manifestations are due to mutations in mitochondrial DNA, but are difficult to diagnose due to the varied clinical picture and the lack of sensitive or specific diagnostic testing. Past efforts to document mtDNA mutations in children believed to have mitochondrial disorders have been hampered by the size of the mitochondrial genome and the presence of numerous benign polymorphisms.

Mitochondria are eukaryotic cytoplasmic organelles where oxidative phosphorylation takes place, and are often termed the 'power plant' of the cell. In animal cells, the mitochondria is the only cytoplasmic organelle that contains DNA. Human mitochondrial DNA (mtDNA) is a circular molecule of about 16,600 nucleotide pairs which encode thirteen of the at least 82 protein subunits of the complexes in the oxidative phosphorylation pathway, both ribosomal RNAs, and all of the 22 transfer RNAs required for mitochondrial protein synthesis. However, the majority of proteins located in the mitochondria are encoded by nuclear DNA (chromosomal DNA) and translated by cytoplasmic ribosomes, and then imported to the mitochondria. Therefore, a "mitochondrial disorder" can be secondary to a mutation in either the nuclear DNA or in the mitochondrial DNA.

The entire human mitochondrial DNA (mtDNA) sequence has been determined (see MITOMAP: Human Mitochondrial Genome Database, Center for Molecular Medicine, Emory University, Atlanta, Ga., USA (1998); Wallace et al. (1995) Report of the committee on human mitochondrial DNA, In: Cuticchia A J (Ed) *Human gene mapping* 1995: A Compendium, Johns Hopkins University Press, Baltimore, pp 910–954 (1995)).

Mitochondrial genetics differ from nuclear (standard or Mendelian) genetics. Virtually all the mtDNA of a zygote is derived from the oocyte, and mtDNA disorders are transmitted by maternal inheritance. Maternal-linked (matrilineal) relatives presumably have identical mtDNA sequences, except perhaps at the site of a new mutation. Additionally, the mtDNA mutation rate is substantially higher than that of the nuclear DNA. Most cells contain hundreds to thousands of mitochondria, and each mitochondria contains several copies of mtDNA, resulting in high mtDNA copy number. In normal individuals, essentially all of the mtDNA molecules are identical (homoplasmy). However, if there is a mutation in mtDNA, the mutant mtDNA and the normal (wild type) mtDNA often coexist in the same cell or tissue (heteroplasmy).

Because of the high mutation rate, mtDNA has numerous polymorphisms. Almost always these polymorphisms are homoplasmic. In contrast, most recognized pathogenic mtDNA mutations are heteroplasmic, especially when disease manifests during childhood (Shoffner and Wallace (1995) In: *The Metabolic and Molecular Basis of Inherited Disease* (7$^{th}$ Ed.), New York, McGraw Hill, 1535–1629).

As a result of segregation in the pre-oocyte stage, each ova of an affected woman has a different proportion of mutant versus normal mtDNA, which can range from virtually 0 to 100%. Each of her children, therefore, will inherit differing amounts of mutant mtDNA. In addition, normal and mutant mtDNA randomly segregate during the cell divisions of embryogenesis, resulting in different proportions of mutant mtDNA residing in different tissues. The presence of clinical disease in a given tissue is dependent on the specific mutation, the percent of mutant mtDNA and the threshold for that tissue. The percentage of mutant mtDNA necessary to cause clinical symptoms varies from tissue to tissue; for example, 80% mutant mtDNA may be clinically silent in liver but cause symptoms in tissues with higher energy requirements, such as muscle or brain (Shoffner et al. (1991) *Adv. Hum. Genet.* 19:267). Since the mutant mtDNA load varies between matrilineal family members, as well as between tissues within each individual, the clinical manifestations of a mtDNA mutation vary widely among affected family members. Healthy family members with mutant mtDNA levels below threshold are common. These individuals, if female, are 'carriers' as their children will inherit their mitochondria and, if inherited mutant mtDNA levels are above threshold, the children will be affected. A well known example is the A3243G mtDNA mutation, in which family subjects exhibit variable manifestations, ranging from stroke (usually associated with relatively higher degrees of mutant heteroplasmy) to those (with lesser mutant loads) with diabetes, deafness, or asymptomatic carriers. This phenomenon of varied clinical presentation has been observed with other mtDNA mutations as well.

As the mtDNA mutation rate is high, mtDNA disorders may be due to new mtDNA mutations; in such cases matrilineal relatives will be unaffected. In other cases, mothers harbor small degrees of mutant heteroplasmy and are clinically normal or only mildly affected. In a minority of cases, multiple matrilineal relatives harbor various amounts of mutant mtDNA in their tissues and exhibit varying clinical manifestations.

A broad spectrum of disease manifestations has been associated with systemic mtDNA mutations. These mutations can be either single point mutations, or large rearrangements (deletions and/or duplications). Rearrangements usually are spontaneous, although they may be maternally inherited or mendelianly inherited secondary to predisposing nuclear mutations.

Clinical mitochondrial dysfunction may be defined as idiopathic neuromuscular and/or multisystem disease, biochemical signs of energy depletion, and lack of another diagnosis. Mitochondrial disorders are evidenced when the cellular supply of energy is unable to keep up with demand; symptoms predominate in tissues with the highest energy requirements (brain and muscle). Mitochondrial disorders are most commonly displayed as neuromuscular disorders, including developmental delay, seizure disorders, hypotonia, skeletal muscle weakness and cardiomyopathy. Other manifestations which have been reported include gastroesophageal reflux, apnea, optic atrophy, deafness, acute liver failure, diabetes mellitus, and other hormonal deficiencies.

Mitochondrial disorders are often not suspected until late in a diagnostic work-up. Confirmation of a mitochondrial disorder is, at present, a time-consuming and expensive process, and may include lactic acid measurement in body fluids and diagnostic muscle biopsy for electron microscopy and assay of the electron transport chain activities in vitro. However, these methods rarely specify the mode of inheritance or allow for presymptomatic or prenatal diagnosis.

SUMMARY OF THE INVENTION

A method of screening a subject for mitochondrial dysfunction is disclosed. The method comprises detecting the presence or absence of single nucleotide changes in a hypervariable region of the mitochondrial DNA of said subject, the presence of such changes indicating that said subject is afflicted with or at risk of developing mitochondrial dysfunction.

Also disclosed is the use of a means for detecting the presence or absence of single nucleotide changes in a hypervariable region of the mitochondrial DNA of a subject in or for determining if that subject is afflicted with or at risk of developing mitochondrial dysfunction.

The foregoing and other objects and aspects of the present invention are explained in greater detail below.

BRIEF DESCRIPTION OF THE DRAWINGS

FIG. 1 shows the pedigrees in patients 1 and 8. Each of the disease manifestations present in these families is consistent with a possible mitochondrial disorder. Squares=males; circles=females; and circles within squares=either gender. Arabic numbers within symbols indicate the number of (normal) individuals. The arrows point to our cases (probands).

FIG. 2 shows an expanded diagram of human mtDNA-CR. The mtDNA-CR is defined as the area flanked by the tRNA genes for proline (tRNA$^{Pro}$) and phenylalanine (tRNA$^{Phe}$) (boxes with diagonal stripes). The location of each heteroplasmic nucleotide found among the cases described herein are marked by black lines and by the nucleotide number. Although not precisely defined, the approximate locations are noted for the hypervariable regions (HV1 and HV2, box with vertical stripes), evolutionary conserved sequence blocks (CSBs, solid boxes), displacement loop (D-loop, open box), the origin of heavy strand replication ($O_H$), and the transcription initiation sites for the 2 heavy strand (H1 and H2) and light strand (L) transcripts (arrows indicating the direction of transcription). The cross-hatched boxes at the bottom of the figure depict the areas screened by each of the PCR-amplified segments described herein.

DETAILED DESCRIPTION OF PREFERRED EMBODIMENTS

The present invention is primarily intended to be carried out on human subjects, including both male and female subjects, of any age, including juvenile subjects. The method may be carried out on subjects who have been previously diagnosed as afflicted with mitochondrial dysfunction, or as a prognostic test on subjects who have not yet been diagnosed as afflicted with mitochondrial dysfunction. The test may be carried out as a screening procedure, wherein a positive result in the test indicates increased risk of mitochondrial dysfunction.

The mtDNA hypervariable region from which changes or mutations indicative of mitochondrial dysfunction generally consists of hypervariable region HV1 and HV2. Any change or mutation set forth in EXAMPLES hereto may be used in carrying out the test.

The changes or mutations described herein may be detected by any suitable technique, including but not limited to DNA amplification techniques such as described in U.S. Pat. No. 5,767,248 to Roses et al., the disclosure of which is incorporated herein by reference, adapted to be carried out on the changes or mutations described herein.

EXAMPLE 1

Inheritance of Mitochondrial Disorders

Children with idiopathic neuromuscular and/or multi-system disease manifestations are frequently encountered in pediatric tertiary practice. Some of these children bear one or more descriptive diagnoses such as mental retardation, epilepsy, migraine or cardiomyopathy. Increasingly, a proportion of these children are found to have biochemical signs of a possible defect in energy metabolism such as an elevated body fluid lactate, abnormal urine organic acids and/or mitochondrial proliferation by enzyme analysis in muscle. Whether these findings represent primary inborn errors of mitochondrial energy metabolism ('mitochondrial disorders') or non-specific secondary phenomenon remains controversial.

Figure 1:
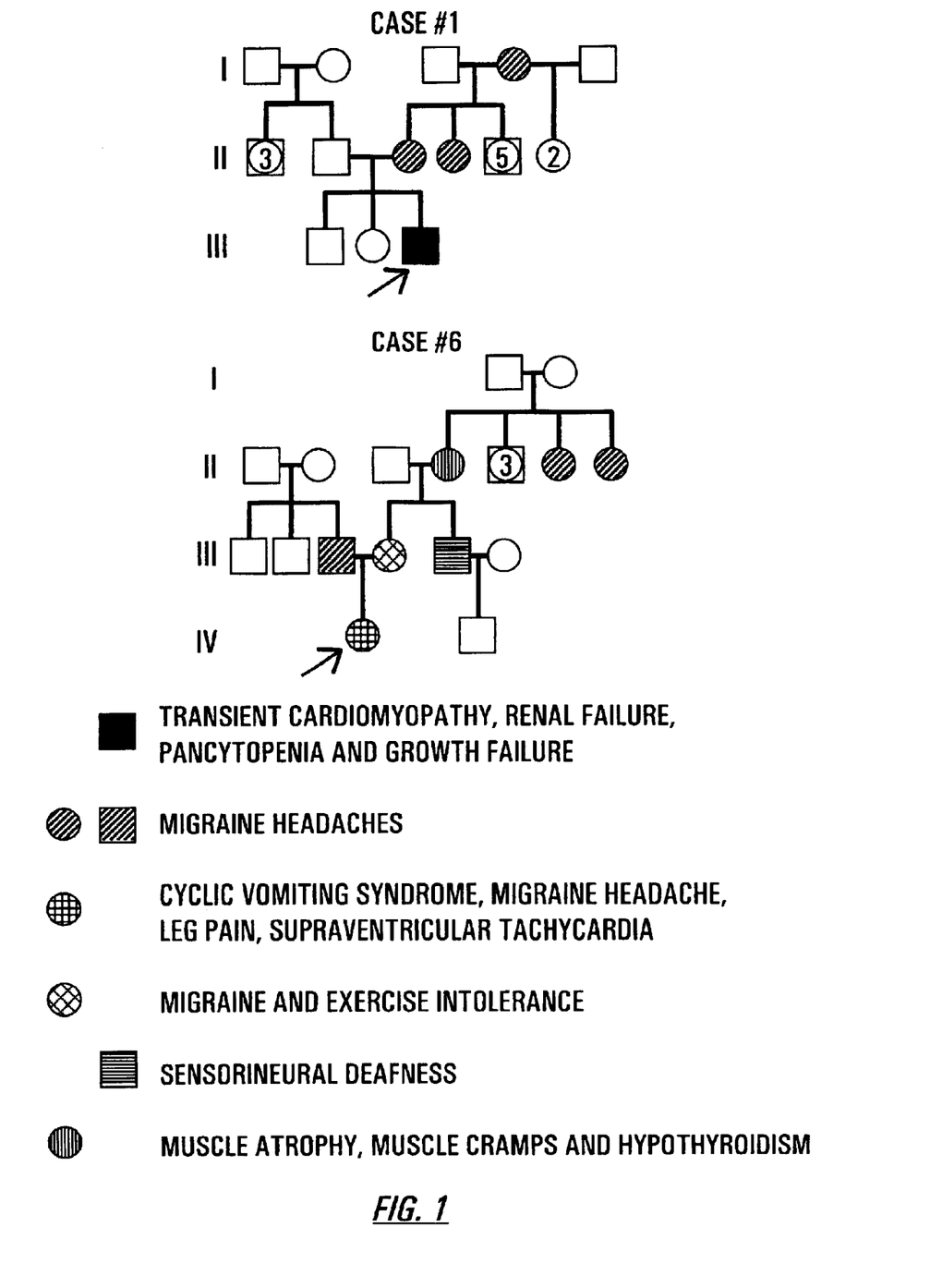

It has been observed that many of these children have matrilineal relatives with widely different, often transient and mild, neuromuscular and/or multi-system manifestations, including migraine (FIG. 1). This observation suggests that a maternally-transmitted factor may be involved in the development of disease manifestations in a substantial proportion of cases. Since mitochondria contain their own DNA (mtDNA) which is maternally transmitted (Shoffner and Wallace (1995) Oxidative phosphorylation diseases. In: Scriver C R, Beaudet A L, Sly W S, Valle D, editors. *The metabolic and molecular bases of inherited disease*, 7th ed. New York: McGraw-Hill, pg 1535–629; Chinnery and Turnbull (1997) *Q J Med,* 190:657–66), mtDNA sequence variations likely constitute this maternally-transmitted factor. However, known mtDNA mutations are infrequently (<5%) identified in children suspected of having a mitochondrial disorder (Liang and Wong (1998) *Am J Med Genet*, 77:395–400), suggesting that additional pathological mtDNA variants remain to be discovered.

Mitochondrial genetics differs in many aspects from Mendelian, or nuclear, genetics. Mitochondrial DNA is a 16,569 base pair circular molecule which encodes 13 protein subunits of the mitochondrial respiratory chain, as well as the 22 transfer RNA and 2 ribosomal RNA genes required for the translation of the mtDNA-encoded proteins (Shoffner and Wallace (1995) Oxidative phosphorylation diseases. In: Scriver C R, Beaudet A L, Sly W S, Valle D, editors. *The metabolic and molecular bases of inherited disease,* 7th ed. New York: McGraw-Hill, pg 1535–629). Mitachondrial DNA exists at high copy number, usually on the order of hundreds or thousands of genomes per cell. Heteroplasmy, defined as the existence of two or more different mtDNA sequences in the same cell, is associated with several, predominantly neuromuscular and/or multi-system disease states in man (Shoffner and Wallace (1995) Oxidative phosphorylation diseases. In: Scriver C R, Beaudet A L, Sly W S, Valle D, editors. *The metabolic and molecular bases of* inherited disease, 7th ed. New York: McGraw-Hill, pg 1535–629; Chinnery and Turnbull (1997) *Q J Med*, 190:657–66). Over 80 different pathological mtDNA point mutations have been described to date, and the vast majority exist in patients in a heteroplasmic state along with wild-type genomes (Shoffner and Wallace (1995) Oxidative phosphorylation diseases. In: Scriver C R, Beaudet A L, Sly W S, Valle D, editors. *The metabolic and molecular bases of inherited disease*, 7th ed. New York: McGraw-Hill, pg 1535–629; Kogelnik et al. (1996) *Nuc Aci Res*, 24:177–9. In contrast, normally occurring mtDNA point sequence variants (polymorphisms) are almost always homoplasmic (only one mtDNA sequence present) (supra). Clinical symptoms occur once the proportion of mutant mtDNA molecules exceeds a threshold which is both tissue and mutation specific (Shoffner and Wallace (1995) Oxidative phosphorylation diseases. In: Scriver C R, Beaudet A L, Sly W S, Valle D, editors. *The metabolic and molecular bases of inherited disease*, 7th ed. New York: McGraw-Hill, pg 1535–629; Chinnery and Turnbull (1997) *Q J Med*, 190:657–66). Partially in response to varying proportions of mutant and wild-type heteroplasmy among different tissues within each individual and among different family members, maternal inheritance is often characterized by widely variable clinical manifestations, age of onset and severity among members of the same family (supra).

As the only large non-coding region in the mitochondrial genome, the approximate 1 kilobase (kb) mtDNA control region (CR) is involved in mtDNA replication, transcription and membrane attachment (FIG. 2) (Shoffner and Wallace (1995) Oxidative phosphorylation diseases. In: Scriver C R, Beaudet A L, Sly W S, Valle D, editors. *The metabolic and molecular bases of inherited disease*, 7th ed. New York: McGraw-Hill, pg 1535–629; Kogelnik et al. (1996) *Nuc Aci Res*, 24:177–9. Control region mutations which interfere with these and other 'regulatory' functions constitute a plausible mechanism for human disease, although disease-causing mutations in this region have not been reported. Within the mtDNA-CR are 2 highly polymorphic regions, termed hypervariable region 1 and 2 (HV1, HV2) (supra). A very common HV1 variant consisting of an expanded homopolymeric tract of cytosines (length heteroplasmy) was recently reported as associated with insulin resistance (Poulton et al. (1998) *Diabetologia*, 41:54–8). The present study shows the presence of multiple heteroplasmic and homoplasmic single nucleotide changes in the hypervariable regions of the mtDNA-CR in 13 of 67 children with idiopathic neuromuscular and/or multi-system disease manifestations and an elevated body fluid lactate concentration.

EXAMPLE 2

Case Reports

Clinical and laboratory findings in each of the 11 children with mtDNA-CR point heteroplasmy patterns on temporal temperature gradient gel electrophoresis (TTGE) are listed in Table 1. Although there is substantial variability in clinical manifestations among the 11 children as a whole, many cases cluster into clinically-based groups, some of which may be syndromic. The following 6 cases were chosen for a more detailed description in order to demonstrate the range of phenotypic expression. Patient 8 was previously reported in brief (Boles and Williams (1999)-*Dig Dis Sci*, 44 (Suppl.):103S–107S. Pedigrees for patients 1 and 8 are shown in FIG. 1.

TABLE 1

|  | Patient #1 | Patient #2 | Patient #3 |
|---|---|---|---|
| Brief Clinical Description | Reversible severe cardiomyopathy | Reversible severe cardiomyopathy | Reversible severe cardiomyopathy |
| Age/Sex/Race | 7/M/B | 4/F/H | 2/F/H |
| Heteroplasmy | 16168C-T | Insufficient DNA | 16093T-C |
| Growth | Failure-to-thrive, Short stature | Early failure-to-thrive | Short stature |
| Developmental Delay | None | None | Mild |
| Seizures | None | None | None |
| Skeletal Muscle | Hypotonia, Weakness, Atrophy | Mild atrophy | Weakness, Fatigue |
| Cardiac Muscle | Dilated cardiomyopathy | Dilated cardiomyopathy | Dilated cardiomyopathy |
| Gastrointestinal | Chronic diarrhea | Normal | Normal |
| Other Clinical | Pancytopenia | None | Hydrops, Congestive failure |
| Clinical Course | Improved | Improved | Improved |
| Highest Lactate | 4.8 mM | 2.0 mM | 2.5 mM |
| Urine Organic Acids | Ketones | Normal once | Krebs cycle, Generalized organic aciduria |
| Cranial Imaging | Not done | Not done | CT: Mild atrophy |
| Muscle Biopsy | Increased variation in muscle fiber sizes, Increased lipid, High citrate synthase, Low complex 1, 3, 4 | Not done | High citrate synthase |
| Family History | Maternal history of migraine | Sporadic | Sporadic |

|  | Patient #4 | Patient #5 | Patient #8 |
|---|---|---|---|
| Brief Clinical Description | Fasting hypoglycemia | Fasting hypoglycemia | Migraine/ dysautonomia |
| Age/Sex/Race | 3/M/C | 4/F/C | 12/F/C |

TABLE 1-continued

| | | | |
|---|---|---|---|
| Heteroplasmy | 16481C-T | Insufficient DNA | 16176C-T<br>16338A-G |
| Growth | Normal | Normal | Normal |
| Developmental Delay | None | None | None/gifted |
| Seizures | Tonic and absence | None | None |
| Skeletal Muscle | Episodes of weakness and muscle cramps, Hypotonia in infancy | Normal | Normal |
| Cardiac Muscle | Normal | Normal | SVT |
| Gastrointestinal | Normal | GER, constipation, multiple episodes of acute abdominal pain | Cyclic vomiting |
| Other Clinical | 3 episodes of hypoglycemia and/or altered mental status with fasting, Chronic fatigue, asthma | Monitored for possible sleep apnea, Hypoketotic hypoglycemia with fasting, ADHD | Dilated left ureter, Leg cramps with exercise |
| Clinical Course | Improved | Improved, except for ADHD | Improved |
| Highest Lactate | 3.5 mM | Normal once | 7.4 mM |
| Urine Organic Acids | Krebs cycle | Lactate, Ketones, Free fatty acids, Glutarate | Lactate, Ketones, Krebs cycle |
| Cranial Imaging | MRI: Increased T2 signal in basal ganglia | Not done | Not done |
| Muscle Biopsy | Not done | Not done | Increased variation in muscle fiber sizes, Increased lipid, High citrate synthase, Low complex 1 |
| Family History | Mildly affected brother | Unknown (adopted) | Maternal |

| | Patient #9 | Patient #10 | Patient #11 |
|---|---|---|---|
| Brief Clinical Description | Mental retardation/spasticity | Neonatal severe multi-system disease | Mental retardation/spasticity |
| Age/Sex/Race | 5/F/H | 0/F/C | 5/M/H |
| Heteroplasmy | 16259C-T<br>16278C-T (mom)<br>16288T-C | 16186C-T | HV2 |
| Growth | Mild short stature | Failure-to-thrive | Short stature, Microcephaly |
| Developmental Delay | Profound | Vegetative | Profound |
| Seizures | Probable as infant | Myoclonic | Brief clonic |
| Skeletal Muscle | Spastic quadriplegia | Hypertonia | Spastic quadriplegia |
| Cardiac Muscle | Normal | Hypertrophic cardiomyopathy, Cardiac arrests | Normal |
| Gastrointestinal | Normal | Esophageal atresia, Severe dysmotility | Severe GER, Upper GI bleeding |
| Other Clinical | Optic atrophy, Strabismus, Nystagmus | Acute renal failure, Multiple infections, Left superior vena cava and aortic arch | Optic atrophy, Cortical blindness Obstructive sleep apnea |
| Clinical Course | Static | Improved, then died | Static |
| Highest Lactate | 3.5 mM | 19 mM | 3.6 mM |
| Urine Organic Acids | Normal once | Lactate, Ketones, Ethylmalonate, Krebs cycle, Generalized organic aciduria | Mild ketones once |
| Cranial Imaging | MRI: Leukodystrophy | CT: Thalamic infarcts | MRI: Ulegyria |

TABLE 1-continued

| | | | |
|---|---|---|---|
| Muscle Biopsy | Not done | Increased variation in muscle fiber sizes, Low complex 1, 4, [High citrate synthase in sibling] | Focal increased mitochondrial staining |
| Family History | Sporadic | Identically affected male and female siblings who died, HV1 heteroplasmy in father | Identically affected male and female siblings who died, First cousin parents |

| | Patient #12 | Patient #13 |
|---|---|---|
| Brief Clinical Description | Reversible multi-system disease | Reversible multi-system disease |
| Age/Sex/Race | 3/F/H | 5/F/H |
| Heteroplasmy | 16215A-T | 16285C-T |
| Growth | Failure-to-thrive, Short stature | Failure-to-thrive, Short stature |
| Developmental Delay | Mild | Mild-moderate |
| Seizures | Complex partial | In infancy only |
| Skeletal Muscle | Hypotonia | Normal |
| Cardiac Muscle | Normal | Normal |
| Gastrointestinal | Pyloric stenosis, GER, DGE | Gastrostomy |
| Other Clinical | Cleft palate | Bronchopulmonary dysplasia, Ventilator dependent |
| Clinical Course | Improved | Improved |
| Highest Lactate | 3.4 mM | 5.4 mM |
| Urine Organic Acids | Lactate, Ketones, Krebs cycle | Ketones, Free fatty acids, Generalized organic aciduria |
| Cranial Imaging | MRI: Normal | Not done |
| Muscle Biopsy | Increased variation in muscle fiber sizes, Increased lipid, High citrate synthase | Not done |
| Family History | Maternal | Maternal |

H = Hispanic (of any race), B = Black/African American, C = Caucasian. Mixed racial children are listed as per their matrilineal race. The racial distribution in our cases resembles that of our referred patient population. The number of substitutions includes only single base pair changes, either homoplasmic or heteroplasmic, and scored as the number found in the patient/ the number found in the paired haplogroup-matched control.
SVT = supraventricular tachycardia, GER = gastroesophageal reflux, DGE = delayed gastric emptying, ADHD= attention deficit hyperactivity disorder. Lactate measurements listed are in plasma; normnal range 0.5–2.2 mM. Urine organic acids were performed by GC/MS; selected elevated species are listed. Kreb cycle = Kreb cycle intermediates, including fumarate, malate, and succinate.
As is common in patients with other mtDNA disorders, in many of our cases normal lactates and organic acids were obtained at times while the child was clinically stable. Normal once = test performed only once and while the child was stable. In patient 4, a plasma acylcamitine profile revealed a low acetylcamitine only.
In patient 5, organic acids showed increased long chain free fatty acids, 3-hydroxy free fatty acids (saturated and unsaturated C10, 12 and 14), and dicarboxylic acids (C6, 8, & 10); fatty acid oxidation disorders were essentially ruled out by normal palmitate and myristate oxidation rates (M. Bennett, Dallas, Texas), normal enzymatic activities for LCHAD, SCHAD and both long and short chain 1-3-ketoacyl-CoA thiolases, molecular testing for the common MCAD mutation and plasma acyl carnitines (showing only a non-specific increase in medium chain species, predominantly unsaturated). Muscle biopsies were performed on quadriceps; selected abnormalities are listed. Citrate synthase is a reference enzyme which when elevated can indicate mitochondrial proliferation.
Low complex 1, 3, and/or 4 refer to abnormal low function of these complexes of the respiratory chain (20–50% of normal activity in each case, except for patient 6). Patient 6 received 3 biopsies at different centers by his parents' request; complex 1 deficiency (1/10th of the 5th % ile) was found by Dr. John Shoffner, Scottish Rite Hospital, Atlanta, while a partial complex 4 deficiency was found by Dr. Richard Haas, University of Califomia San Diego, both on fresh muscle.
As complexes 1, 3 and 4 contain mtDNA-encoded subunits, partial deficiency of each is consistent with a mtDNA mutation. Complex 5 (also containing mtDNA-encoded subunits) was not measured.

Patient 1 [Transient severe cardiomyopathy]. This child had an unremarkable history until at age 8 months a spider bite became infected which was followed by a loss of developmental milestones. At age 1.5 years an apparent viral upper respiratory and gastrointestinal illness with fasting and dehydration progressed to metabolic acidosis, pancytopenia and dilated cardiomyopathy with congestive heart failure. Developmental delay and failure-to-thrive (FTT) were noted at that time. A mitochondrial disorder was suspected and the child received symptomatic treatment and fasting avoidance. All clinical problems resolved within the next few months except for cyclic neutropenia, which resolved before his third birthday. Currently, at age 7 the child is clinically completely normal, including school performance and cardiac function, except for stable and symmetrical growth retardation (height age=4.7 years). The pedigree is shown in FIG. 1.

Patient 2 [Transient severe cardiomyopathy]. This child presented at age 6 months with severe dilated cardiomyopathy in congestive heart failure. She was medically treated and listed for transplantation, however, her cardiac function markedly improved on strict fasting avoidance and standard medical therapy. At age 4.5 years she has near normal systolic function and possible mild decreased diastolic function. Mild failure-to-thrive also resolved. Intelligence and physical examination are normal except for a decreased muscle bulk. The family history is unremarkable.

Patient 4 [Fasting hypoglycemia]. At the age of 13 months, following 10 days of upper respiratory tract symptoms with decreased oral intake, this child was found to be hypoventilating, gray, staring and limp, progressing rapidly to posturing and coma. Temperature was 34.9° C. and serum glucose was 2.2 mM (40 mg/dl) when paramedics arrived; all symptoms resolved immediately following the administration of a glucose-containing intravenous fluid. A very similar event occurred following an eight-hour overnight fast. A disorder of fatty acid oxidation was postulated and fasting precautions were initiated, including 3–4 hours feedings by day and continuous drip feedings by night. No further episodes have occurred, although the child has not been fasted. Gross motor delay, mild hypotonia and growth retardation resolved. At present, the child is asymptomatic except for asthma, occasional staring spells and rare episodes of profound muscle weakness and flank/leg pain during which the child is unable to bear weight for about 2 hours. Family history is remarkable only for a cystic hygroma and similar episodes of muscle weakness, generalized fatigue and an inability to walk in his now 5 year old brother. Their normal parents are not consanguineous.

Patient 9 [Mental retardation/spasticity]. This child has a static encephalopathy with profound mental retardation, spastic quadriplegia, strabismus and nystagmus. Signs or symptoms of non-neuromuscular tissue dysfunction have been absent. Diagnostic evaluation revealed optic atrophy and leukodystrophy. The family history is unremarkable.

Patient 10 [Neonatal severe multi-system disease]. This child presented at birth with esophageal atresia and a severe metabolic acidosis refractory to standard treatment. He was transported to the Childrens Hospital Los Angeles facility in severe cardiogenic shock at age 11 days and started on ionotropes for a hypertrophic cardiomyopathy, peritoneal dialysis for acute renal failure and specific therapy for mitochondrial failure. The latter was designed in order to reverse and prevent catabolism and consisted of a continuous infusion of glucose at 10–12 mg/kg/min, insulin at about 0.1 units/kg/hr (titrated to maintain serum glucose between 5–10 mM=90–180 mg/dl), and protein at 1.0 g/kg/d. On this treatment, the anion gap (30 to 14 mM), plasma lactate and renal function normalized, and cardiac function greatly improved within one week. Of note, the lactate remained elevated for several days following the return of normal circulation. The child remained ventilator dependent with chronic lung disease and suffered several cardiac arrests; the last one being lethal at age 4 months. The family history is remarkable for a previous male and female sibling with very similar manifestations (including organic acids and muscle electron transport chain activities in one), who died at ages 3 and 5 months despite intensive support.

Patient 12 [Reversible multi-system disease]. This child was delivered at 28 weeks gestation following a pregnancy reportedly complicated by cocaine and ethanol exposure, although facial morphology appears normal. However, except for chronic lung disease and brief mixed apnea, there were no other complications related to prematurity. The child's first year was dominated by severe symmetrical FTT and gastrointestinal dysfunction; a fundoplication/gastrostomy and pyloroplasty were performed for gastroesophageal reflux (GER) and pyloric stenosis. Additional problems included complex partial seizures, hypotonia and cleft palate. All of these conditions either resolved or were surgically repaired, and presently at age 3 years her only problem is mild global cognitive delay. Although she remains very small (height and weight age=17 and 13 months, respectively), she now demonstrates a normal growth rate for age. The child was adopted, although her 4 year old maternal half-sister was evaluated and found to have symmetrical FTT with a normal current growth rate, moderate developmental delay, strabismus, and resolved GER.

EXAMPLE 3

Methods

Subjects. The experimental group consisted of 67 unrelated children ascertained over a five year period (1994–1999) from the clinical genetics practice of Dr. Richard Boles at Childrens Hospital Los Angeles. All qualifying children were retrospectively recruited based upon the presence of neuromuscular and/or multi-system system disease, an elevated body fluid lactate concentration (usually in plasma and often minimally elevated, >2.0 mM or 18 mg/dl) and the absence of another diagnosis despite an extensive evaluation. This latter evaluation was tailored to each specific child, but always included a high resolution karyotype, urine organic acids, plasma amino acids, Southern blotting for large rearrangements, and PCR for 10 known point mutations (Wong and Senadheera (1997) *Clin Chem* 43:1857–61). An additional 14 children that would have qualified were excluded from the study due to the absence of available DNA from a blood sample. No cases were included if ascertainment was based on the referral of a sample to the laboratory for the purpose of mtDNA analysis.

The control group consisted of 103 unrelated individuals, of which 76 were children of all ages, with definitive diagnoses of non-mitochondrial disorders, including 58 individuals with phenylketonuria (PKU) diagnosed on newborn screening, and 33 and 12 individuals diagnosed by molecular assays with spinal muscular atrophy and Duchenne muscular dystrophy, respectively. There was no reason to believe that any of these conditions were related to mtDNA sequence variations. This study was approved by the CHLA Institutional Review Board.

Figure 2:
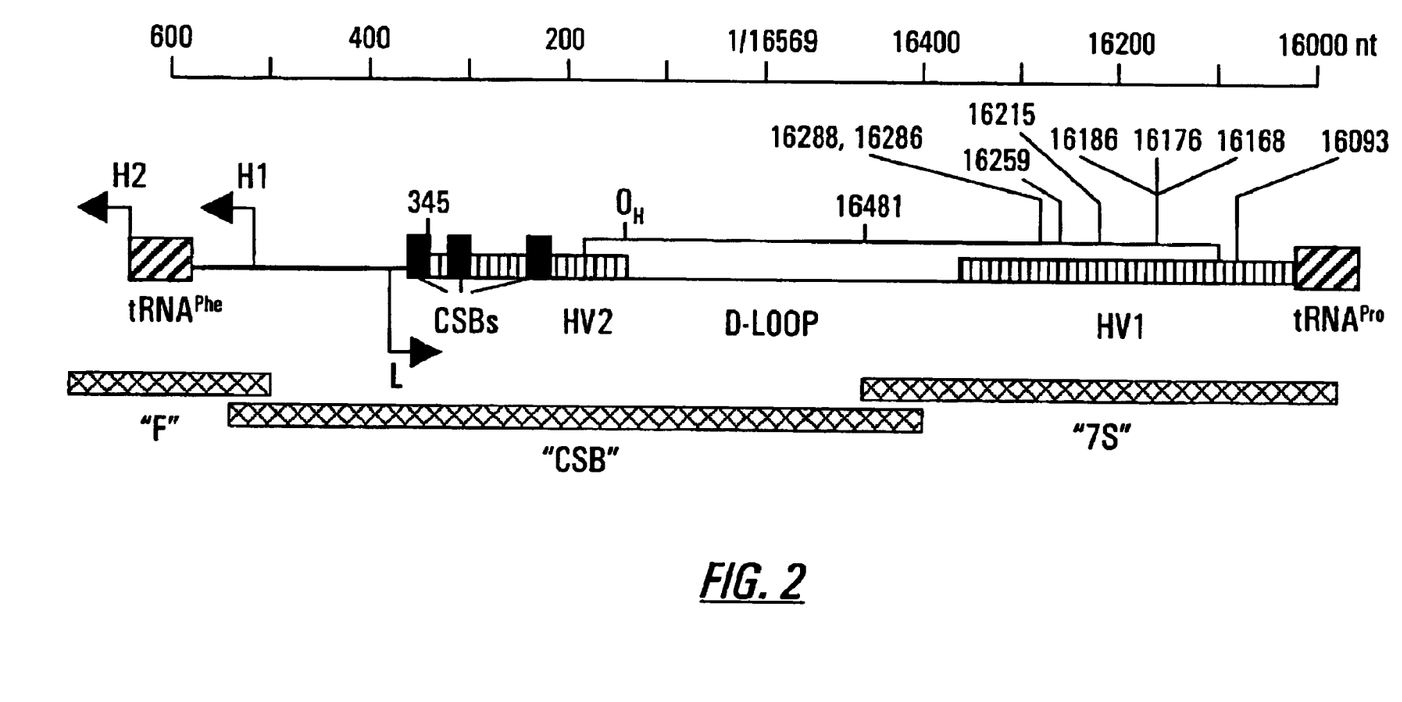
Figure 3:
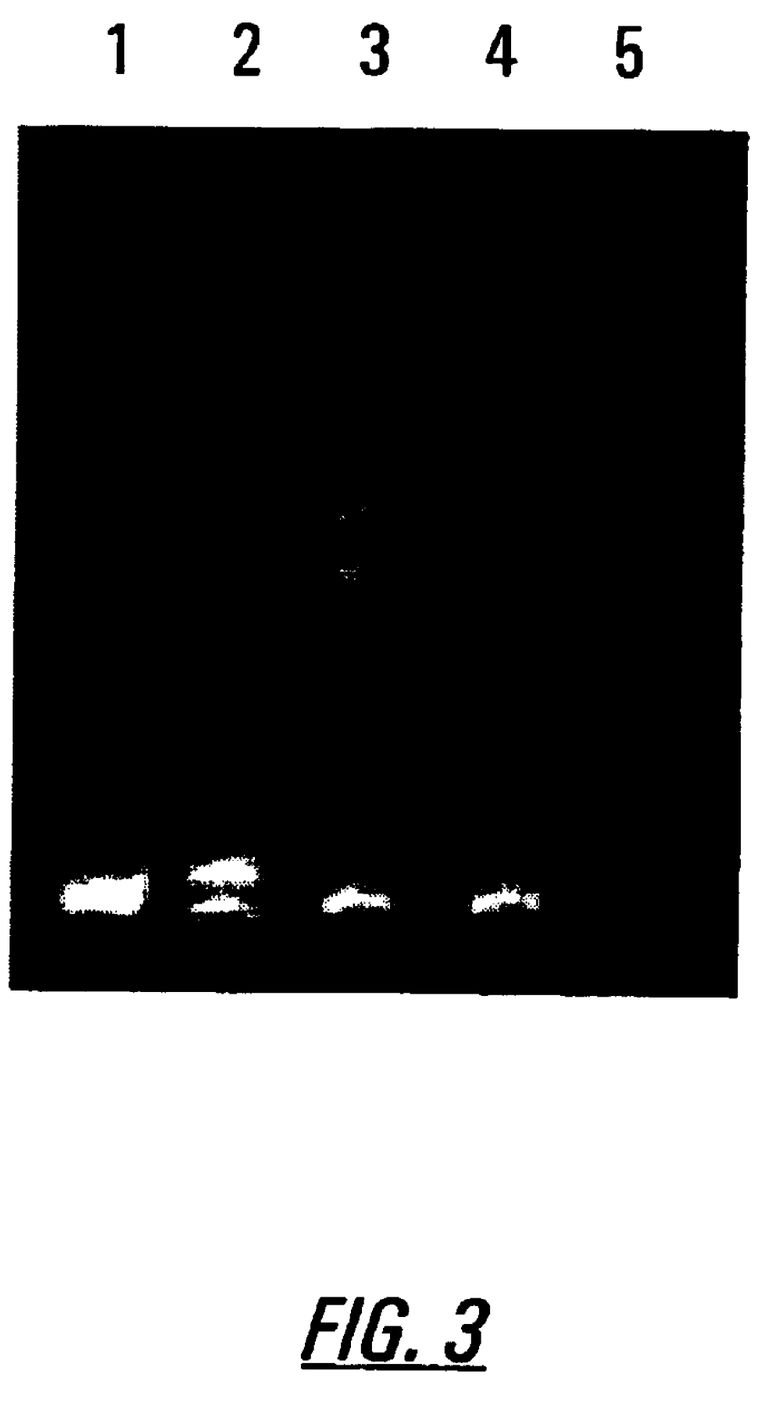
FIG. 3 shows a computer scanned image of a TTGE gel of the 7S segment in 5 unrelated individuals: a normal control (lane 1), a child with length heteroplasmy at 16184 (lane 2), two subjects with different point heteroplasmic variants (lanes 3 & 4), and rho negative cell culture (lane 5). As shown here, in the absence of heteroplasmy (homoplasmy) a single distinct band is seen on the gel, while heteroplasmic samples usually demonstrate 3 or 4 bands on TTGE, corresponding to the predicted 2 homoduplex and 2 heteroduplex species (often the homoduplex bands are not separated).

Molecular Assays. Total DNA was extracted from blood or hair root and PCR and temporal temperature gradient gel electrophoresis (TTGE) were performed as previously reported (Zoller and Redilla-Flores (1996) Temporal temperature gradient gel electrophoresis of cystic fibrosis samples on the Dcode system. Bio-Rad Laboratories, US/EG Bulletin 2103; Chen et al. (1999) *Clin Chem* 45:1162–7; Higashimoto et al. (1999) *Clin Chem* 45:2005–6; Wong and Lam (1997) *Clin Chem* 43:1241–3). Peripheral blood was assayed in all cases and controls. When available, hair was assayed in the probands and blood and/or hair was assayed in their first degree relatives. The mtDNA control region was divided into 3 segments for TTGE analysis (FIG. 2). TTGE was a relatively novel heteroduplex detection assay which has been shown to be very sensitive in the detection of mtDNA heteroplasmy (including 60 of 60 known cases positively identified (Chen et al. (1999) *Clin Chem* 45:1162–7; Chen et al. (1997) *Am J Hum Genet* 61:A306 (abstract)). TTGE was also very specific as each heteroplasmic mutation or polymorphism demonstrated a reproducible and distinct band pattern (FIG. 3) (Chen et al. (1999) *Clin Chem* 45:1162–7). Heteroplasmy could be detected with proportions as low as about 5% (supra). Ethidium bromide stained TTGE gels were visualized under UV light and imaged with a digital CCD gel documentation system. Percent heteroplasmy for each sequence variant could readily be estimated by the relative intensities of the bands. These measurements could be taken by eye or Gene scan analysis with fluorescent labeled primers and employing the binomial theorem, with results closely agreeing those obtained by denaturing high performance liquid chromatography (Transgenomic WAVE™ DNA Fragment Analysis System, Omaha, Nebr., data not shown).

For quality assurance, every gel was run concurrently with 1–3 positive controls (known heteroplasmic samples). All assays were repeated starting with the original extracted DNA sample in every case in which heteroplasmy was found in order to exclude PCR artifacts. Pseudogenes were not amplified in any of the segments as determined by the absence of any PCR product (FIG. 3) using primers listed in Table 2 with total DNA extracted from rho negative cell culture (cells lacking any mtDNA (Chomyn et al. (1991) *Mol Cell Biol* 11:2236–44), kindly provided by Anne Chomyn at CalTech). Contaminated (i.e. blood transfused) samples were easily detected by the presence of multiple bands (>4) present in multiple mtDNA segments. One such sample was thus identified and removed from this study after confirmation of contamination by HLA typing. Cyclosequencing was performed in all cases with multiple bands seen on TTGE either from a single band cut out from the gel or directly from the original samples, using a dye terminator Cyclosequencing kit (Applied Biosystems) and an Applied Biosystems ABI 373A DNA Sequencer. Haplogrouping was determined by restriction digest and sequencing part of the control region as previously reported (Torroni et al. (1996) *Genetics* 144:1835–50).

TABLE 2

| Segment | mtDNA Regions | Nucleotides | Size (bp) | Primer Sequences (5'–3') | Ta | Ti-Tf, Tr |
|---|---|---|---|---|---|---|
| 7S | Control region (includes HV1); tRNA-Pro | 15987–16509 | 523 | upper CACCCAAAGCT AAGATTCTAA (SEQ ID NO:1) lower AGGCTTTATGAC CCTGAAGTA (SEQ ID NO:2) | 53 | 50–62, 3.0 |
| 7Sb* | Control region | 16200–16509 | 310 | upper TCCACATCAAAA CCCCCCCCC (SEQ ID NO:3) lower AGGCTTTATGAC CCTGAAGTA (SEQ ID NO:4) | 53 | 56–64, 3.0 |
| 7Sc* | Control region | 15852–16155 | 304 | upper TCTCCCTAATTG AAAACAAAA (SEQ ID NO:5) lower TGGATTGGGTTT TTATGTACT (SEQ ID NO:6) | 58 | 50–59, 3.0 |
| CSB | Control region (includes HV2) | 16407–560 | 723 | upper CCTCCGTGAAAT CAATATCCC (SEQ ID NO:7) lower AAACTGTGGGG GGTGTCTTTG (SEQ ID NO:8) | 53 | 54–61, 3.7 |
| F | Control region tRNA-Phe; 12S-rRNA | 500–1190 | 691 | upper CCCATCCTACCC AGCACACAC (SEQ ID NO:9) lower GATATGAAGCA CCGCCAGGTC (SEQ ID NO:10) | 56 | 55–59, 1.0 |

TTGE conditions for each segment were determined by computer simulation (MacMelt, Bio-Rad Laboratories) and adjusted by experimentation. $T_a$ is the annealing temperature for PCR. $T_1$, $T_f$, and $T_r$ are the initial, final, and ramp rate temperatures for TTGE.
*A common length heteroplasmy at nt 16184 in the 7S segment occasionally complicated the search for potential additional point heteroplasmies elsewhere in the same segment. These cases were each evaluated by TTGE in two additional segments '7Sb' and '7Sc' which excluded the site of the length heteroplasmy by moving one of the primer sites to a conserved sequence area close to the homopolymeric cytosine tract.

EXAMPLE 4

Results

Distinct TTGE band patterns consistent with the presence of a heteroplasmic single nucleotide substitution ('point heteroplasmy', FIG. 3) were found in the 7S fragment in 10 of 67 children in the experimental group and in none of the 103 individuals in the control group (p<0.001). In the 8/10 cases in which sufficient DNA was available, sequencing confirmed the presence of at least one point heteroplasmy in hypervariable region 1 (HV1, Table 1, FIG. 2; one mutation was outside of the region commonly referred to as HV1). TTGE analysis in the CSB fragment was consistent with point heteroplasmy in 1 case and in 0 controls; and sequencing revealed a heteroplasmic nucleotide in HV2 (Table 1, FIG. 2). In each case, these base substitutions were previously identified in homoplasmic form as polymorphisms (found in normal individuals) (Kogelnik et al. (1996) *Nuc Ad Res*, 24:177–9; Opdal et al. (1998) *Acta Paediatr* 87:1030–44), and many of these polymorphisms have been encountered upon sequencing control individuals in the laboratory (data not shown). Elsewhere in the mtDNA control region, point heteroplasmy was absent in all patients and controls. Multiple cases in both the experimental and control groups were revealed by TTGE and confirmed by sequencing to have polymorphic length variants (length heteroplasmy). Most of these length variants have been previously reported (Bendall and Sykes (1995) *Am J Hum Genet* 57:248–56; Torroni et al. (1994) *Am J Hum Genet* 55:760–76), although rare or unique variants were also found in at least 2 patients and are the subject of continuing investigation.

In order to determine whether the observed point heteroplasmic variants were inherited or somatic mutations, samples were assayed from the family members of patients. Consistent with maternal inheritance of mtDNA, in each case in which samples from the mother (patients 4, 6–10, 13), full sibling (patients 4, 6, 9, 10, 13) or maternal half sibling (patient 12) were available, the identical point heteroplasmy was identified by TTGE and/or sequencing. Samples were available from the fathers of patients 1, 4, 6, 7, 9 and 10 and the specific nucleotide variation seen in the proband was absent in each. A distinct HV1 point heteroplasmy was noted in the father of patient 10. DNA was not available from any family members of the child with HV2 heteroplasmy.

Direct sequencing of the patient or family samples rarely reveals heteroplasmy due to low proportions of the minority sequence (often about 5–25% as estimated by TTGE). The methods employed herein, which involve sequencing of DNA derived from different gel bands, readily reveals the two sequences constituting the heteroplasmic nucleotide identified by TTGE, but this does not exclude the presence of other heteroplasmic nucleotides within the same segment. Careful review of the HV1 sequences revealed probable point heteroplasmy in additional nucleotides in many cases, but not in controls. A second heteroplasmic nucleotide, suspected by sequencing, was confirmed using PCR/allele specific oligonucleotide (ASO) analysis (Wong and Senadheera (1997) *Clin Chem* 43:1857–61) in patients 8 and 9 (Table 1). In the latter, further PCR/ASO analyses in the asymptomatic (by history and neurological examination) mother and 11 year old sister revealed the presence of point heteroplasmy at both nucleotides in the mother, and at one site only in the sister (16288T-C). In addition, a third point heteroplasmy was found in the mother, which was homoplasmic for the polymorphism (16278T) in our patient by PCR/ASO. At each heteroplasmic loci, the proportions of each variant were widely different in each family member (and in individual hair roots within each individual), such that almost all direct sequences revealed homoplasmy (single mtDNA sequence present) for one or the other sequence variant.

In conclusion, reported herein is a novel association of predominantly intermittent and non-progressive disease, biochemical signs suggestive of mitochondrial dysfunction, and maternally-inherited mtDNA-CR point heteroplasmy. Pathology is likely mediated through a novel disease mechanism. This disorder is apparently not rare as it was identified in 1/6 children with idiopathic neuromuscular or multisystem disease and an elevated body fluid lactate, a paradigm which is frequently seen in tertiary practice. With highly variable manifestations, this condition(s) will likely be encountered by clinicians in a variety of specialties treating children. Recognition is important, not only to provide the family with a specific diagnosis that in cases without severe neuromuscular disease appears to carry a relatively favorable prognosis, but in many cases to provide appropriate treatment, especially regarding the avoidance of fasting.

The foregoing is illustrative of the present invention, and is not to be construed as limiting thereof. The invention is defined by the following claims, with equivalents of the claims to be included therein.

We claim:

1. A method of screening a subject for risk of developing mitochondrial dysfunction, comprising detecting the presence or absence of one or more heteroplasmic single nucleotide substitutions in hypervariable region HV1 of the mitochondrial DNA of said subject, wherein the presence of said one or more substitutions indicates that said subject is at risk of developing mitochondrial dysfunction.

2. The method according to claim 1, wherein said subject is a human subject.

3. The method according to claim 1, wherein said single nucleotide change is selected from the group consisting of:
   16168 C-T,
   16093 T-C,
   16176 C-T,
   16259 C-T,
   16278 C-T,
   16288 T-C,
   16186 C-T,
   16215 A-T, and
   16235 C-T.

4. The method according to claim 1, wherein said single nucleotide substitution is 16168 C-T.

5. The method according to claim 1, wherein said single nucleotide substitution is 16093 T-C.

6. The method according to claim 1, wherein said single nucleotide substitution is 16176 C-T.

7. The method according to claim 1, wherein said single nucleotide substitution is 16259 C-T.

8. The method according to claim 1, wherein, said single nucleotide substitution is 16278 C-T.

9. The method according to claim 1, wherein said single nucleotide substitution is 16288 T-C.

10. The method according to claim 1, wherein said single nucleotide substitution is 16186 C-T.

11. The method according to claim 1, wherein said single nucleotide substitution is 16215 A-T.

12. The method according to claim 1, wherein said single nucleotide substitution is 16285 C-T.

13. A method of screening a subject for risk of developing mitochondrial dysfunction, comprising detecting the presence or absence of heteroplasmic single nucleotide substitutions in the mitochondrial DNA of said subject, wherein the heteroplasmic single nucleotide substitution is selected from the group consisting of 16168 C-T, 16093 T-C, 16481 C-T, 16176 C-T, 16388 A-G, 16259 C-T, 16288 T-C, 16186 C-T, 16215 A-T, 16285 C-T, and combinations thereof, wherein the presence of one or more of said substitutions indicates that said subject is at risk of developing mitochondrial dysfunction.

* * * * *

UNITED STATES PATENT AND TRADEMARK OFFICE
CERTIFICATE OF CORRECTION

PATENT NO. : 6,759,196 B2
DATED : July 6, 2004
INVENTOR(S) : Boles et al.

It is certified that error appears in the above-identified patent and that said Letters Patent is hereby corrected as shown below:

<u>Column 20,</u>
Line 21, should read -- C-T, 16176 C-T, 16388 A-G, 16259 C-T, 16278 C-T, 16288 T-C, 16186 --

Signed and Sealed this

Fourteenth Day of June, 2005

JON W. DUDAS
*Director of the United States Patent and Trademark Office*